United States Patent [19]

Jaeger et al.

[11] Patent Number: 4,812,344
[45] Date of Patent: Mar. 14, 1989

[54] COMPOSITE CAPILLARY TUBE STRUCTURE AND METHOD OF FORMING

[75] Inventors: Raymond E. Jaeger; Mohd Aslami, both of Sturbridge, Mass.

[73] Assignee: Spectran Corporation, Sturbridge, Mass.

[21] Appl. No.: 173,952

[22] Filed: Mar. 28, 1988

[51] Int. Cl.⁴ ............................................. C03B 23/13
[52] U.S. Cl. ..................................... 428/34.6; 65/36; 65/54; 65/87; 65/102; 428/427
[58] Field of Search ................. 65/36, 54, 86, 87, 102; 428/36, 427

[56] References Cited

U.S. PATENT DOCUMENTS

| | | | |
|---|---|---|---|
| 1,547,715 | 7/1925 | Baker | 65/36 |
| 2,052,269 | 8/1936 | Woods | 49/17.1 |
| 2,313,296 | 3/1943 | Lamesch | 65/86 X |
| 3,190,735 | 6/1965 | Kapany | 65/102 X |
| 3,455,666 | 7/1969 | Bazinet, Jr. | 65/4 |
| 3,960,530 | 6/1976 | Iyengar | 65/3 C |
| 4,022,603 | 5/1977 | Roeder et al. | 65/145 |
| 4,023,953 | 5/1977 | Megles, Jr. et al. | 65/86 |
| 4,368,063 | 1/1983 | Presby | 65/42 |
| 4,428,764 | 1/1984 | Snitzer et al. | 65/102 |
| 4,437,727 | 3/1984 | Treber | 428/36 |

FOREIGN PATENT DOCUMENTS 496281 2/1937 United Kingdom ............... 65/54

*Primary Examiner*—Arthur Kellogg
*Attorney, Agent, or Firm*—Pennie & Edmonds

[57] ABSTRACT

A composite capillary tube structure made of a plurality of glass layers and methods for making same. This composite includes inner and outer layers of fused silica glass separated by an intermediate layer of a glass material having a higher coefficient of thermal expansion than the fused silica glass. The glass material of the intermediate layer also has a glass transition temperature on the same order as that of fused silica, so that the fused silica layers are maintained under compressive forces over a temperature range of up to about 400° C. Preferably, the intermediate layer is a borosilicate or aluminosilicate glass.

16 Claims, 1 Drawing Sheet

COMPOSITE CAPILLARY TUBE STRUCTURE AND METHOD OF FORMING

TECHNICAL FIELD

This invention relates to novel constructions of composite capillary tubing.

BACKGROUND ART

Fused silica capillary tubing has substantially replaced rigid, soft-glass capillaries as the separation column used in gas chromatography. This material offers higher strength, more flexibility, easier connect/disconnect capability, and a chemically inert inner surface for stationary phase application. It is typically used in 10 to 50 meter lengths wound in 15 to 20 cm diameter coils. Capillary bore diameters vary approximately from 0.01 to 0.6 mm with wall thicknesses in the range of 0.025 to 0.100 mm.

To better withstand handling and because the column is often heated in use in order to affect a better separation of unknown sample constituents, the silica capillary requires a strength protective coating that is able to withstand intermittent temperatures up to 400° C. A polyimide material has been used for this purpose because it is one of the few classes of polymers able to withstand these temperatures.

The capillary is typically produced by heating the end of a relatively large diameter fused silica tube to its softening point and drawing the soft glass, thus reducing its size to capillary dimensions. The process is made continuous by slowly advancing the tube into the hot zone while simultaneously continuing to draw capillary out, the volume rate moving into the hot zone being equal to the volume rate being drawn out. The polyimide coating is applied in liquid form and cured to a polymerized solid in-line during the drawing process.

The combination of capillary tube diameter and coiled column diameter results in varying degrees of in-situ tensile stress in portions of the tube. Since the plymer coating is not impervious to water vapor, with time and repeated temperature cycling during use, the column ultimately fails mechanically as a result of the action of static fatigue on those capillary surfaces experiencing tensile stress. The present invention provides a simple capillary tube construction in which a stress balance is achieved that eliminates or reduces tensile stress on the capillary surfaces thus limiting the effect of static fatigue and resulting in a longer useful column life.

SUMMARY OF THE INVENTION

The invention relates to composite capillary tube structure made of a plurality of glass layers comprising inner and outer layers of a first glass material separated by an intermediate layer of a second glass material having a higher coefficient of thermal expansion than that of the first glass material, so that upon cooling from the softening temperature, the inner and outer layers are placed in compression.

The inner, intermediate and outer layers are bonded to each other. The second or intermediate glass transition temperature as close as possible to that of the first glass material, with a strain point preferably above the maximum temperature the column will be exposed to in use (approximately 400° C.).

Advantageously, the outer layers of this composite capillary tube structure are fused silica while the intermediate layer is a borosilicate, aluminosilicate or other glass composition having the desired properties.

The invention also relates to a method of making a composite capillary tube structure having a plurality of glass layers, which method comprises forming a preform of concentric tubes comprising inner and outer layers of a first glass material separated by an intermediate layer of a second glass material having a higher coefficient of thermal expansion than that of the first glass material; heating the preform to a sufficient temperature to soften the glass materials; drawing a composite capillary tube structure from the heated preform; and cooling the tube structure to develop stresses between the layers, so that upon subsequent heating, the inner and outer layers are maintained under compressive forces over a temperature range of up to about 400° C.

This method also includes drawing the tube from the preform so that the inner, outer and intermediate layers are bonded to each other.

Preferably, the intermediate layer is selected from glasses having a glass transition temperature which is between about 500 degrees and the glass transition temperature of the inner and outer layers.

An advantageous material for the inner and outer layers for most applications is fused silica, while the intermediate layer can be a borosilicate, aluminosilicate or other glass composition having the desired properties.

Another aspect of the invention relates to the composite capillary tube structures produced by the above-described method.

BRIEF DESCRIPTION OF THE DRAWINGS

The nature, advantages, and various other additional features of the invention will appear more fully upon consideration of the illustrative embodiments now to be described in detail in connection with the accompanying drawing figures, wherein.

DESCRIPTION OF THE PREFERRED EMBODIMENTS

The invention relates to capillary tubing composite structures designed to place the inner and outer glass surfaces under compression in the as-drawn condition. The level of compression can be designed such that when coiled in its final configuration both inner and outer surfaces are either in a reduced tensile stress condition or at some predetermined level of compression.

Where both inner and outer surfaces are in compression, the design is analogous to tempered glass or prestressed reinforced concrete. Thus, compressively stressed capillary surfaces would render the tubing more resistant to physical abuse, such as mechanical impact that would normally result in tensile forces acting to proprogate surface cracks. In addition, stress corrosion will be reduced, thus yielding a longer useful life to the column. Also, for the situation where the intermediate layer of glass has a higher thermal coefficient of expansion than the outer layer over the entire temperature range anticipated during operation of the capillary, the composite provides resistance to thermal cycling, since the outer and inner surfaces are maintained under compression over the entire anticipated temperature range.

Figure 1:
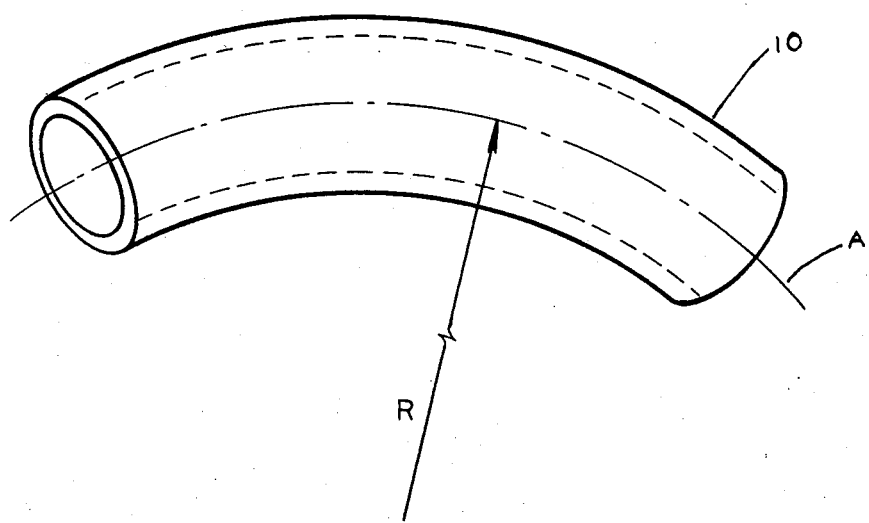
FIG. 1 is a perspective view of a capillary tube being stressed by bending along radius R.

Consider a capillary tube 10 having axis A, an inside diameter of about 0.25 mm and an outside diameter of 0.35 mm. This tube 10 is wound in a 15 cm coil of radius R as shown in FIG. 1. In this coiled configuration, the axis of the tube becomes the neutral stress axis. In the bent tube, that portion of the glass wall outside the neutral axis is being stretched while that portion of the glass wall inside the neutral axis is being shortened. This causes the surfaces outside the axis to be in tension and those inside the axis to be in compression.

The axial tensile stress on the glass surfaces outside the neutral axis is given approximately by formula I as follows:

$$\sigma = (E)(d)/(D) \qquad \text{I}$$

Where:
$\sigma$ = stress
E = Elastic Modulus of the material
d = capillary diameter
D = coil diameter The stress would then be $$\sigma = \frac{10^7 \times 35 \times 10^{-3}}{15} = 23{,}000 \text{ psi}$$

of tension acting on the outer and inner surfaces of the tube 10 which lie outside the tube axis. In this stressed condition, and further with time and temperature cycling, the capillary tube 10 is subject to static fatigue, that is, an environmentally accelerated subcritical micro-crack growth that ultimately leads to failure. If all the tube surfaces are maintained under compression or reduced tension, they would be less subject to this phenomenon of surface crack growth.

Figure 2:
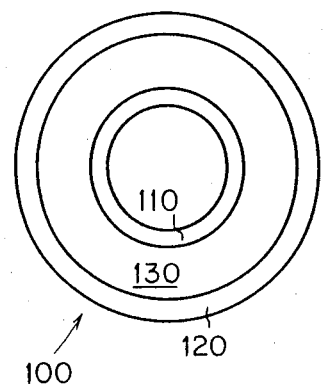
FIG. 2 is a top view of a capillary tube structure according to the invention.
Figure 3:
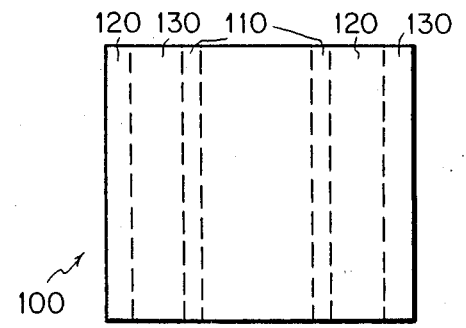
FIG. 3 is a side view of the capillary tube of FIG. 2.

In FIG. 2, a composite capillary tubing structure 100 according to the invention is shown. The material which forms the inside 110 and outside 120 surface layers would typically be pure fused silica. Fused silica has a glass transition temperature of about 1000° C., a thermal expansion coefficient of about $3 \times 10^{-7}$ °C.$^{-1}$, and a modulus of elasticity of about $7 \times 10^6$ psi. A material having a higher coefficient of thermal expansion than silica and a glass transition temperature ($T_g$) as high and as close to silica as possible is used to form an intermediate layer 130 which is sandwiched between these silica layers. Other material combinations meeting the criteria proposed here are also possible.

The new composite capillary 100 can be drawn from a preform having the same structure prepared using a variety of well known CVD techniques or from concentric tubes of the appropriate glass compositions. Upon cooling, during the draw process, stresses will develop when the temperature of the composite cools below the $T_g$ of layer 130 (assuming it has the lower $T_g$). At room temperature, a tensile stress in layer 130 (having no free exterior surface) is balanced by a compression in the material used for the inside and outside layers; 110 and 120.

With complete bonding at the interface between these materials, the composite displacement will be constrained by the material with the higher elastic modulus. For the situation where the total cross sectional areas of each of the two different materials are equal and the capillary wall is very thin, a one dimensional analysis of the axial stress can be applied. The composite stress will be controlled by the differential strain and the lower of the two moduli according to formula II as follows:

$$\sigma = (E)(\Delta\alpha)(\Delta T) \qquad \text{II}$$

where:
$\sigma$ = Tensile or Compressive Stress
E = The lower Elastic Modulus of the two materials
$\Delta\alpha$ = Differential Expansion of the two materials
$\Delta T$ = Difference between the lower $T_g$ value and room temperature

EXAMPLES

The scope of the invention is further described in connection with the following examples which are set forth for the sole purpose of illustrating the preferred embodiments of the invention and which are not to be construed as limiting the scope of the invention in any manner.

Example 1

A Corning borosilicate glass (code 7740) is used as the material of layer 130. This glass has a glass transition temperature of 510° C., a thermal expansion coefficient of $35 \times 10^{-7}$ °C.$^{-1}$, and a modulus of elasticity of about $9 \times 10^6$ psi. Then, according to formula II above:

$$\sigma = 9 \times 10^6 \text{ psi} \times 3.2 \times 10^{-6} \times 490$$

or about 14,000 psi compression at the free surfaces of layers 110 and 120 at room temperature.

Example 2

The material of layer 130 is a Corning Aluminosilicate glass (code 4720) having a glass transition temperature of about 667° C., a thermal expansion coefficient of about $52 \times 10^{-7}$ °C.$^{-1}$, and a modulus of elasticity of about $10 \times 10^6$ psi. Then formula II shows that the stress is:

$$\sigma = 10 \times 10^6 \text{ psi} \times 4.9 \times 10^{-6} \times 647$$

or about 31,700 psi compression at room temperature.

Using the combination of the glass of Example 1 or 2 as the inner layer for a 15 cm coiled 0.35 mm outside diameter capillary column described earlier in FIG. 1, would produce a minimum compression of about 7,000 and 15,500 psi, respectively, for the inner and outer layers. The column would therefore exhibit superior static fatigue properties. By using CVD techniques to prepare this tube, the properties of the composite can be tailored to different tubing sizes, column diameters and maximum use temperatures.

While it is apparent that the invention herein disclosed is well calculated to fulfill the objects above stated, it will be appreciated that numerous embodiments and modifications may be devised by those skilled in the art, and it is intended that the appended claims cover all such modifications and embodiments as fall within the true spirit and scope of the present invention.

We claim:

1. A composite capillary tube structure made of a plurality of glass layers comprising:
   inner and outer layers of a first glass material separated by an intermediate layer of a second glass material having a higher coefficient of thermal expansion than that of said first glass material, so that the inner and outer layers are maintained under a compressive force over a temperature range of up to about 400° C.

2. The composite capillary tube structure of claim 1 wherein the second glass material has a glass transition temperature between 500° C. and the $T_g$ of said first glass material.

3. The composite capillary tube structure of claim 2 wherein the glass transition temperature of the second glass material is as close as possible to that of said first glass material.

4. The capillary tube structure of claim 1 wherein the outer layer is fused silica.

5. The tube structures of claim 1 wherein the intermediate layer is a borosilicate or aluminosilicate glass.

6. A composite capillary tube structure made of a plurality of glass layers comprising inner and outer layers of fused silica glass separated by an intermediate layer of a glass material having a higher coefficient of thermal expansion than said fused silica glass, said glass material also having a glass transition temperature on the same order as that of fused silica, so that the fused silica layers are maintained under compressive forces over a temperature range of up to about 400° C.

7. The capillary tube structure of claim 6 wherein the intermediate layer is a borosilicate or aluminosilicate glass.

8. A method of making a composite capillary tube structure having a plurality of glass layers, which method comprises:
    forming a preform of a concentric tube comprising inner and outer layers of a first glass material separated by an intermediate layer of a second glass material having a higher coefficient of thermal expansion than that of said first glass material;
    heating said preform to a sufficient temperature to soften the glass materials;
    drawing a composite capillary tube structure from said heated preform; and
    cooling said tube structure to develop stresses between said layers, so that the inner and outer layers are maintained under compressive force over a temperature range of up to about 400° C.

9. The method of claim 8 which further comprises selecting said intermediate layer having a glass transition temperature which is within about 100 degrees of that of said inner and outer layers.

10. The method of claim 8 which further comprises selecting said inner and outer layers of fused silica.

11. The method of claim 8 which further comprises selecting said intermediate layer of a borosilicate or aluminosilicate glass.

12. A method of making a composite capillary tube structure having a plurality of glass layers, which method comprises:
    forming a preform of a concentric tube comprising inner and outer layers of fused silica separated by an intermediate layer of a glass material having a higher thermal expansion coefficient than that of fused silica;
    heating said preform to a sufficient temperature to soften the glass materials;
    drawing a composite capillary tube structure having said layers bonded together from said heated form; and
    cooling said tube structure to develop stresses between said layers, so that the inner and outer fused silica layers are maintained under a compressive force over a temperature range of up to about 400° C.

13. The method of claim 12 which further comprises selecting said intermediate layer of a borosilicate or aluminosilicate glass.

14. The composite capillary tube structure produced by the method of claim 8.

15. The composite capillary tube structure produced by the method of claim 12.

16. The composite capillary tube structure produced by the method of claim 13.

* * * * *